United States Patent [19]
Barr et al.

[11] Patent Number: 5,868,727
[45] Date of Patent: Feb. 9, 1999

[54] SANITARY ABSORBENT ARTICLE WITH AN ADHESIVE POSITIONING SYSTEM COVERED BY RELEASE STRIPS LINKED TO ONE ANOTHER AND METHOD AND APPARATUS FOR PACKAGING THE ABSORBENT ARTICLE

[75] Inventors: James P. Barr, Columbia, Md.; Marc Alary, Montreal; Henri Brisebois, Lachenaie, both of Canada; Paul Lefebvre, Kiel, Germany; Anita Dupressoir, Montreal, Canada

[73] Assignee: Johnson & Johnson Inc., Montreal, Canada

[21] Appl. No.: 729,521

[22] Filed: Oct. 10, 1996

Related U.S. Application Data

[63] Continuation of Ser. No. 490,970, Jun. 15, 1995.

[51] Int. Cl.$^6$ ............................................. A61F 13/15
[52] U.S. Cl. ................................. 604/387; 604/390
[58] Field of Search .................... 206/446; 604/387, 604/389, 378, 390, 391, 385.1, 386

[56] References Cited

U.S. PATENT DOCUMENTS

| | | | |
|---|---|---|---|
| 4,505,706 | 3/1985 | Erpicum et al. | 604/389 |
| 4,589,876 | 5/1986 | Van Tilburg . | |
| 4,701,178 | 10/1987 | Glaug et al. . | |
| 4,759,754 | 7/1988 | Korpman | 604/389 |
| 5,133,704 | 7/1992 | Wheeler | 604/390 |
| 5,358,499 | 10/1994 | Seidy | 604/387 |

FOREIGN PATENT DOCUMENTS

| | | | |
|---|---|---|---|
| 962805 | 2/1975 | Canada | 604/389 |
| 0 472 376 | 2/1992 | European Pat. Off. | 604/389 |
| 5-108275 | 11/1994 | Japan | 604/389 |
| 2248397 | 9/1991 | United Kingdom | 604/389 |
| 92 04000 | 3/1992 | WIPO | 604/389 |
| 94 04111 | 3/1994 | WIPO | 604/389 |
| 94 27540 | 12/1994 | WIPO | 604/390 |
| 94 27542 | 12/1994 | WIPO | 604/386 |

Primary Examiner—Mark O. Polutta
Assistant Examiner—Ki Yong O
Attorney, Agent, or Firm—James P. Barr

[57] ABSTRACT

A sanitary napkin with laterally projecting positioning tabs. The adhesive securement system of the sanitary napkin includes three adhesive zones in a spaced apart relationship, namely one zone on the main body of the sanitary napkin and one zone on the undergarment facing surface of each positioning tab. A quick-remove peelable protective layer covers the adhesive zones when the sanitary napkin is not in use. The protective layer includes a primary release strip extending longitudinally on the sanitary napkin to cover the adhesive zone on the main body and a transverse secondary release strip overlaying the adhesive zones on the positioning tabs. This arrangement allows removal of entire protective layer in a single peel-off stroke. The invention also relates to a method and apparatus for folding a positioning tab of the sanitary napkin over its main body during a packaging operation that inserts the sanitary napkin in a disposable pouch. The method comprises the steps of creating a crease in the transverse release strip of the protective layer, near the juncture between the positioning tab and the main body of the sanitary napkin. The transverse release strip is made of sufficiently rigid paper material so the crease maintains the positioning tab in a folded condition during the packaging operation.

19 Claims, 7 Drawing Sheets

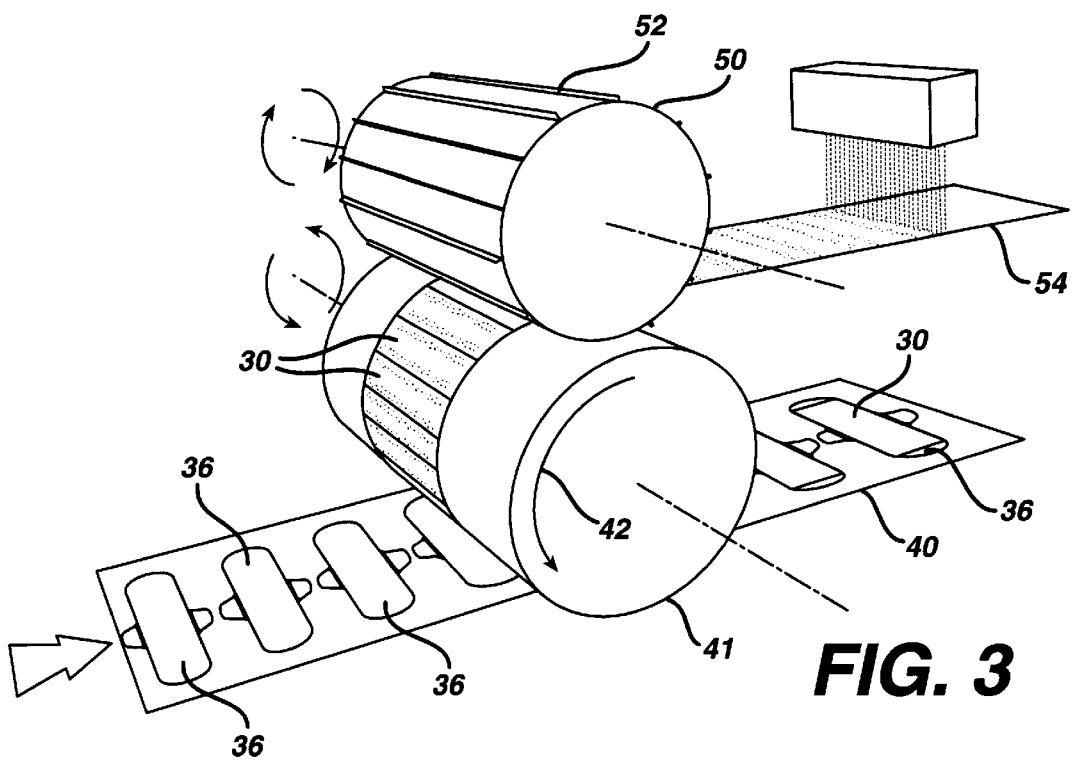
FIG. 3
FIG. 3A
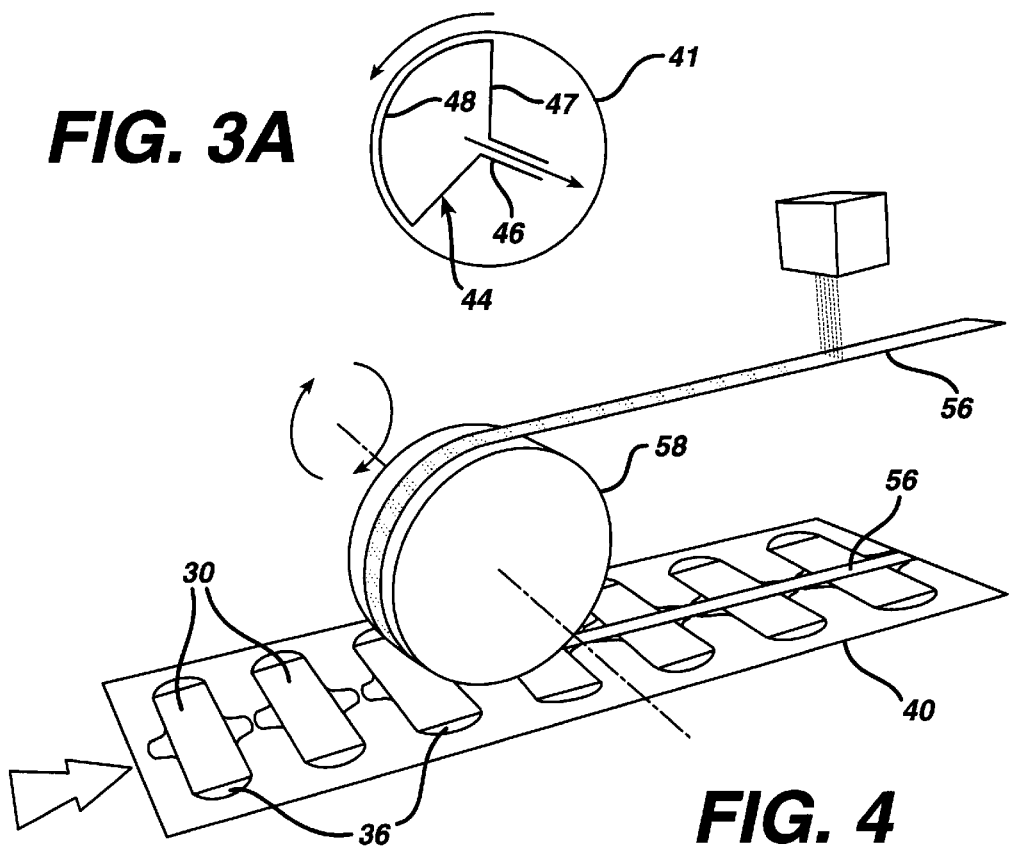
FIG. 4

SANITARY ABSORBENT ARTICLE WITH AN ADHESIVE POSITIONING SYSTEM COVERED BY RELEASE STRIPS LINKED TO ONE ANOTHER AND METHOD AND APPARATUS FOR PACKAGING THE ABSORBENT ARTICLE

This is a continuation of application Ser. No. 08/490,970, filed Jun. 15, 1995.

FIELD OF THE INVENTION

The present invention relates to the art of manufacturing structures for absorbing body exudate and, more particularly, to a disposable sanitary absorbent article with a quick-remove protective layer shielding the adhesive securement system of the absorbent article when the latter is not in use. The invention also extends to a method and apparatus for folding the absorbent article.

BACKGROUND OF THE INVENTION

Disposable absorbent articles, such as sanitary napkins, are maintained against the perineal region of the wearer by adhesively securing the sanitary napkin to the crotch portion of the undergarment. The adhesive securement system usually comprises a plurality of adhesive zones distributed on the barrier layer which create a bond with the undergarment material to maintain the sanitary napkin in place in spite of movements and compression forces acting on it particularly when the wearer is walking or otherwise shifting the position of her legs.

In the past recent years, the industry has designed sanitary napkins with laterally projecting positioning tabs intended to be folded about respective edges of the undergarment for more positively holding the sanitary napkin in place. To develop an effective retention force, the positioning tabs are adhesively secured to the garment facing surface of the underpants. Thus, the sanitary napkin has at least three adhesive zones namely one zone on the main body of the sanitary napkin and two additional adhesive zones one on each positioning tab. To protect the adhesive system while the sanitary napkin is not in use, the manufacturer typically applies a protective layer over each adhesive zone, which is peeled-off by the user immediately prior the placement of the sanitary napkin on the undergarment. The protective layer is generally made of paper having an outer non-stick surface. A particularly useful material is a semi-bleached Kraft paper, the adhesive contacting side of which has been silicone-treated to provide easy release properties.

Some difficulty arises with this approach in that a plurality of separate protective layers are necessary, one for each adhesive zone. Thus, the user is required to separately peel-off several paper strips to expose the entire adhesive system, which is time-consuming and annoying. In addition, the paper strips must be peeled-off with some degree of care to avoid the adhesive zones from contacting each other or the barrier layer of the sanitary napkin. If such an accident occurs, the product can be rendered useless especially if the exposed adhesive on a positioning tab contacts the adhesive zone on the main body of the sanitary napkin.

OBJECTS AND SUMMARY OF THE INVENTION

An object of the invention is a sanitary absorbent article with a protective layer for the adhesive system that can be quickly and conveniently removed.

Another object of the invention is a novel method and apparatus for folding the sanitary article to ease packaging.

As embodied and broadly described herein, the invention provides a disposable sanitary absorbent article for adhesive securement to an undergarment of a wearer, said absorbent article comprising:

a main body that includes:
   a) a body contacting liquid-pervious cover layer;
   b) an absorbent core underneath said body contacting liquid-pervious cover layer, said absorbent core being in liquid-communicative relationship with said cover layer, whereby liquid discharged on said cover layer is transferred to said absorbent core for storage therein;
   c) a liquid-impervious barrier layer beneath said absorbent core, said barrier layer preventing liquid entrapped in said absorbent core from egressing from said main body from a garment facing surface thereof;

a positioning tab laterally projecting from each longitudinal side of said main body, each said positioning tab being flexible and being capable of being folded about a respective edge of an undergarment on which said absorbent article is to be installed;

an adhesive securement system for releasably retaining said absorbent article to the undergarment, said adhesive securement system including;
   a) a first adhesive zone on a garment facing surface of said main body;
   b) a second adhesive zone on a garment facing surface of one of said positioning tabs;
   c) a third adhesive zone on a garment facing surface of the other one of said positioning tabs, said first, second and third adhesive zones being in a spaced apart relationship;
   d) a peelable protective layer covering said adhesive zones, said peelable protective layer including:
      i) a primary release strip extending generally longitudinally on said main body and being releasably attached to said first adhesive zone;
      ii) a secondary release strip extending generally transversely on said main body and being releasably attached to said second and third adhesive zones, said release strips crossing each other.

In a preferred embodiment, the sanitary absorbent article, such as a sanitary napkin, includes a primary release strip extending longitudinally on the main body of the sanitary napkin to cover the first adhesive zone that in use bonds with the body facing surface of the undergarment. Most preferably, the first adhesive zone is formed by a pair of longitudinally extending adhesive bands running almost the entire length of the main body. The secondary release strip is mounted transversely on the sanitary napkin, overlying the primary strip to cover the adhesive zones on the positioning tabs with its end portions. By pulling the primary release strip, the secondary release strip is removed as well to expose the entire adhesive system in a single peel-off stroke. A reverse arrangement where the primary release strip overlays the secondary release strip is also possible. Under this embodiment the user needs to pull on the secondary strip to effect the removal of the entire protective layer.

To prevent the central portion of the uppermost release strip (the point of reference for "uppermost" is a sanitary napkin with a barrier layer on top) from sagging or bowing, it is proposed to adhesively secure both release strips at their crossing point.

The application of the protective layer during the manufacture of the sanitary napkin is a two-step operation. In a most preferred embodiment, the sanitary napkins are directed by a conveyor system to a first processing station that deposits a primary release strip on each sanitary napkin. At this point the sanitary napkins have not yet been cut into individual products and they are still serially united, thus forming a continuous web. The first processing station comprises a vacuum roll immediately above the conveyor belt, which is supplied with release strip material in continuous form drawn from a supply reel. An adhesive applicator deposits hot-melt glue on the run of release strip material between the supply reel and the vacuum roll. The adhesive-coated release strip material is clamped against the circumference of the vacuum roll and transversely cut thereon in discrete primary release strips. The continuing rotation of the vacuum roll which is timed with the linear speed of the conveyor belt deposits the release strips on the sanitary napkins. The hot-melt adhesive is transferred to the barrier layer of each sanitary napkin and permanently bonds with it so when the release strip is peeled-off the adhesive will remain on the barrier layer.

The secondary release strip is applied at a second processing station by the intermediary of a roll that transfers a continuous band of adhesive-coated release strip material to the web containing the sanitary napkins. Note that in addition to depositing on the release strip material the adhesive that will be transferred to the positioning tabs, an additional adhesive site is created to bond the secondary release strip to the underlying primary release strip at their crossing point. Contrary to the process taking place at the first processing station no cutting of the release strip material takes place on the roll. The continuous band of release material is separated in individual release strips later at a die cutting station where the sanitary napkins web is cut in individual products.

To manufacture sanitary napkin with a protective layer where the primary release strip overlays the secondary release strip the same procedure is observed with the exception that the order of deposition of the strips is reversed, i.e. the secondary strip is applied first followed by the primary release strip.

As embodied and broadly described herein the invention also provides a method for folding a sanitary absorbent article which includes a release strip covering an adhesive zone of said sanitary absorbent article, said release strip manifesting a shape retention capability when creased, said method comprising the steps of:

folding said sanitary absorbent article; and forming a crease in said release strip at a fold region of said sanitary article, whereby said release strip assists said sanitary absorbent article in maintaining a folded condition by resisting efforts tending to uncrease said release strip.

In this specification the expression "folding said sanitary absorbent article" should be construed to mean the action of placing one part of the sanitary absorbent article over another part of it, without any limit as to relative size or dimensions of the parts. Thus, folding the sanitary absorbent article in half, or folding only a small part, such as a positioning tab, over the main body would fall in the ambit of this wording.

The expression "shape retention capability" refers to a material that after being deformed has a tendency to remain in the deformed condition.

The expression "folded condition" used subsequently in the text designates the relationship between parts of the sanitary napkin brought by folding movement one over the other and forming an angle between them that is substantially less than 180°.

The folding operation broadly defined above is particularly useful during the packaging operation of the sanitary napkins when they are folded for insertion in disposable pouches. The packaging operation is a delicate procedure because the sanitary napkins once folded have immediate tendency to unfold which makes the insertion of the product in the pouch difficult. Creasing the release strip overcomes this potential difficulty because the release strip material is permanently deformed and it will then oppose the natural tendency of the sanitary napkin to unfold. Thus, the sanitary napkin is maintained in a folded condition for a period sufficiently long to complete the packaging operation.

It should be noted that the folding and the creasing operations can be effected at different instants in time or simultaneously. In the former case, the folding operation is performed first, followed be the creasing operation that permanently deforms the release strip.

In a most preferred embodiment, the folding operation begins by laying one positioning tab over the body contacting liquid-pervious cover layer. A convenient way of folding the positioning tabs is by directing a jet of compressed air at the sanitary napkin to bring the positioning tab in a folded condition. While the air jet is active, the sanitary napkin passes under a creasing roller that creates enough pressure to form a sharp ridge in the release strip. Since the release strip is united to the folded positioning tab and to the remaining part of the sanitary napkin, it will keep the positioning tab folded without any noticeable manifestation of shape recovery over several hours. In practice, it suffices to maintain the positioning tab folded for a time long enough to enable the packaging station to insert the sanitary napkin in the individual pouch. Given the high speed of the machines available today, this time frame is short, in the range of a fraction of a second to a few seconds at most.

The ability of the release strip to resist the natural tendency of the sanitary napkin to unfold depends primarily upon two factors. First, the release strip material must have a shape retention property so once creased it will not immediately return to its original configuration. Second, the material should be sufficiently rigid. The silicone coated paper material that is typically used in the prior art for manufacturing release strips satisfies these requirements. It works particularly well for maintaining the positioning tabs on the sanitary napkin folded against the cover layer. It should be noted that the positioning tabs are thin structures and the force required to keep them in a folded condition is small. Thus, a thin release strip material is sufficient. One could also envisage folding the sanitary napkin at a much thicker region, such as folding it in half which requires bending the entire absorbent system sharply. For such applications, thicker release strip material will be required to maintain the sanitary napkin in a folded condition since it now manifests much higher resiliency.

As embodied and broadly described herein the invention also provides a method of folding a sanitary absorbent article that includes:

a) at least one tab projecting from a main body of said sanitary absorbent article; and b) a release strip covering an adhesive zone of said sanitary absorbent article, said release strip extending over a juncture between said tab and said main body and manifesting a shape retention capability when bent, said method comprising the step of folding said tab over said main body at said juncture to a degree sufficient for causing said release strip to acquire a lasting folded condition, whereby said release strip resists efforts tending to unfold said tab.

The expression "lasting folded condition" means that the release strip will not readily return to its original configuration. Two specific possibilities fall in the ambit of this expression. First, the release strip has very little memory and it remains permanently folded. Second, the release strip is capable of shape recovery, however, the shape recovery is slow. Thus, when the force that bends the release strip is discontinued the release strip remains folded for an appreciable amount of time and does not immediately spring back to its original (non folded) condition. For example, the "lasting folded condition" can be acquired by creasing the release strip.

As embodied and broadly described herein, the invention also provides an apparatus for folding a sanitary absorbent article which includes a release strip covering an adhesive zone of said sanitary absorbent article, said release strip manifesting a shape retention capability when creased, said apparatus comprising:

means for folding said sanitary absorbent article; and means for forming a crease in said release strip at a fold region of said sanitary absorbent article, whereby said release strip assists said sanitary absorbent article in maintaining a folded condition by resisting efforts tending to uncrease said release strip.

In a most preferred embodiment, the means for folding the sanitary absorbent article and the means for creasing are different devices, such as the air jet and the creasing roll described earlier. However, one may envisage combining the folding and the creasing functions together so these operations are performed simultaneously. A possible example is a roller that would fold the sanitary absorbent article and crease the resilient strip at the same time.

As embodied and broadly described herein the invention also provides an apparatus for folding a sanitary absorbent article that includes:

at least one tab projecting from a main body of said sanitary absorbent article; and a release strip covering an adhesive zone of said sanitary absorbent article, said release strip extending over a juncture between said tab and said main body and manifesting a shape retention capability when bent, said apparatus comprising means for folding said tab over said main body at said juncture to a degree sufficient for causing said release strip to acquire a lasting folded condition, whereby said release strip resists efforts tending to unfold said tab.

As embodied and broadly described herein, the invention also provides a sanitary absorbent article including an adhesive zone for securing said sanitary absorbent article to an undergarment of a wearer and a release strip covering said adhesive zone, said sanitary absorbent article being in a folded condition and said release strip including a crease in a folded region of said sanitary absorbent article, said release strip manifesting a shape retention capability when creased, whereby said release strip assists said sanitary absorbent article in maintaining a folded condition by resisting efforts tending to uncrease said release strip.

As embodied and broadly described herein, the invention also provides a sanitary absorbent article including:

a) at least one tab extending from a main body of said sanitary absorbent article, said tab being folded over said main body; and b) a release strip covering an adhesive zone of said sanitary absorbent article, said release strip extending over a juncture between said tab and said main body, said release strip being folded at said juncture and manifesting a sufficient shape retention capability for resisting efforts tending to unfold said tab.

BRIEF DESCRIPTION OF THE DRAWINGS

FIG. 3 is a perspective view of a processing station for applying to sanitary napkins a first component of the protective layer;

FIG. 3A is a schematical cross-sectional view of a vacuum roll from the processing station shown in FIG. 3;

FIG. 4 is a perspective view of a second processing station for applying to the sanitary napkins a second component of the protective layer;

DESCRIPTION OF A PREFERRED EMBODIMENT

Figure 1:
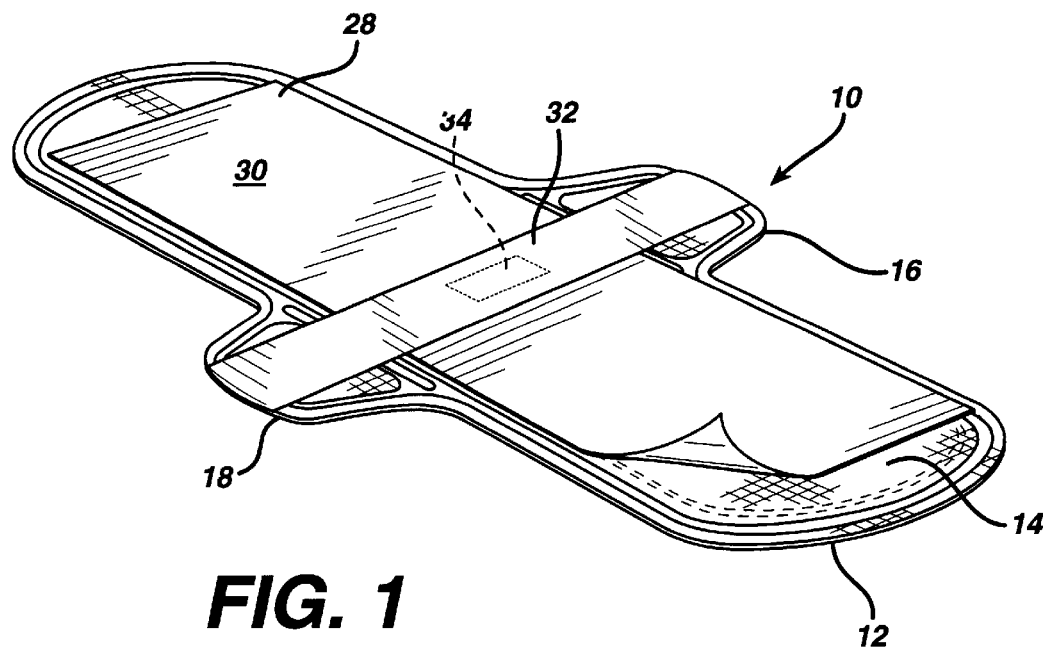
FIG. 1 is a perspective view of a sanitary napkin in accordance with the invention featuring a quick-remove protective layer for the adhesive system.
Figure 2:
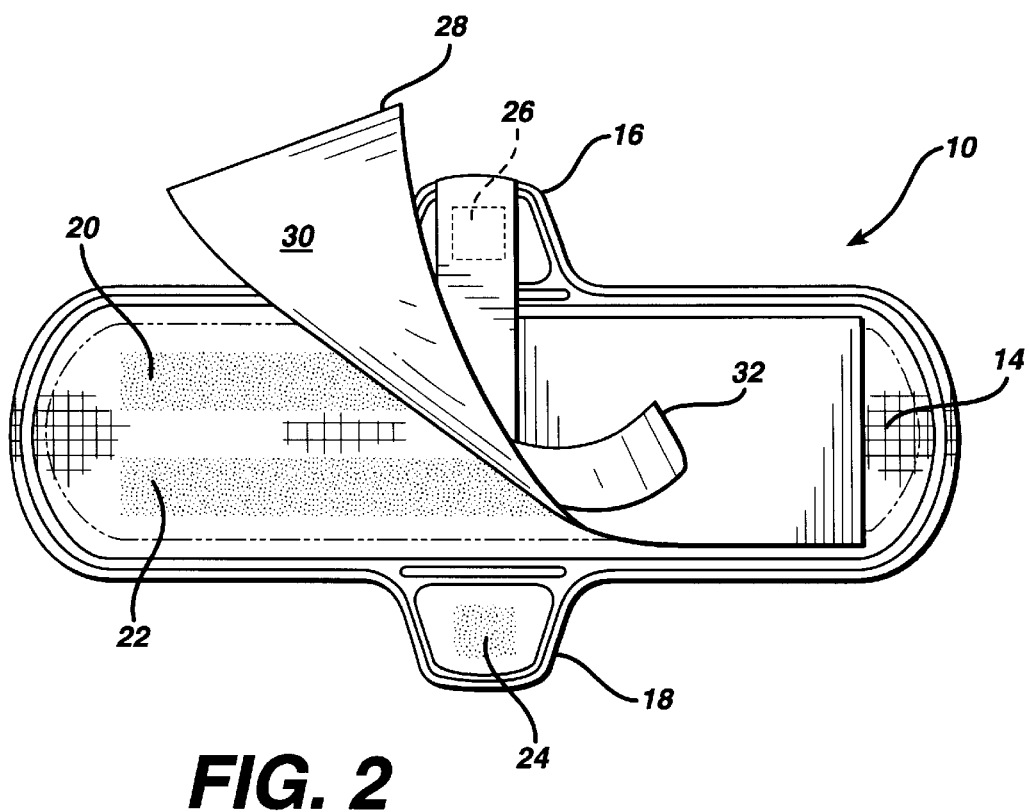
FIG. 2 is a top plan view of the sanitary napkin shown in FIG. 1, the protective layer being shown partly peeled-off.

The present invention provides a sanitary absorbent article, such as a sanitary napkin, having a peelable protective layer that is releasably attached to the adhesive system, which can be removed quickly and conveniently as a single piece. With reference to the annexed drawings, the sanitary napkin designated comprehensively by the reference numeral 10 comprises a liquid-permeable cover layer 12 overlaying an absorbent core (not shown in the drawings). The absorbent core preferably includes sphagnum moss material and it is comparatively thin, i.e., having a few millimeters in thickness. The cover layer is highly porous to allow liquid delivered on the surface of the sanitary napkin to rapidly reach the absorbent core. Underneath the absorbent core is provided a barrier layer 14 made of liquid-impervious material, such as polyethylene, to prevent liquid entrapped in the absorbent core from egressing the sanitary napkin and staining the wearer's undergarment. The cover layer 12 and the barrier layer 14 are joined along their marginal portions to form an enclosure that maintains the absorbent layer with the absorbent core captive. The joint may be made by means of adhesives, heat-bond, mechanical crimping or any other suitable process. Note that in FIGS. 1 and 2 the sanitary napkin 10 is shown in an inverted position; its normal position of use being such that the cover layer 12 is on top and the barrier layer 14 is on the bottom.

To stabilize the sanitary napkin on the wearer's underpants, a pair of laterally projecting positioning tabs 16 and 18 are provided on each longitudinal side edge of the sanitary napkin. The positioning tabs 16 and 18 are dual-layer laminated structures. The upper layer is formed by an extension of the cover 12 and the lower layer by an extension of the barrier layer 14. The positioning tabs 16 and 18 are flexible so they can be folded about the edges of the undergarment.

To secure the sanitary napkin 10 against the undergarment of the wearer, an adhesive securement system is provided comprising a pair of adhesive zones 20 and 22 on the barrier layer of the main body of the sanitary napkin. The adhesive zones 20 and 22 are in the form of elongated bands slightly spaced apart from one another. The bands extend almost the entire length of the sanitary napkin. In addition, the adhesive securement system comprises adhesive zones 24 and 26 on the positioning tabs portions of the barrier layer 14.

To protect the adhesive securement system while the sanitary napkin is not used, a peelable protective layer 28 covers the adhesive zones. The protective layer comprises a primary release strip 30 that extends longitudinally on the sanitary napkin and has a width sufficient to span the adhesive bands 20 and 22. To shield the adhesive zones 24 and 26 on the positioning tabs, a secondary release strip 32 is placed transversely on the sanitary napkin, thus crossing the primary strip 30.

The preferred material for making the release strips 30 and 32 is bleached Kraft paper coated with silicone on the adhesive facing surface to provide a non-sticky side. The release paper material available from the Akrosil Corporation (a division of International Paper) having a basis weight of 25 pounds per ream with a silicone coat of 2.8 pounds per ream has been found satisfactory.

To prevent the central portion of the secondary strip 32 from sagging or bowing when the sanitary napkin is handled, it is adhered to the back surface of the primary strip 30 by means of an adhesive zone 34. This is a very weak bond since one of the surfaces is a silicone coating, however, it has been found sufficient for keeping the secondary strip 32 from freely moving.

To install the sanitary napkin 10, it suffices to peel-off the protective layer 28. This is done by removing first the main release strip 30. By doing so, the secondary release strip 32 is also removed. As a result, the entire adhesive system is exposed in a single peel-off stroke which is quick and convenient for the user.

The sanitary napkin 10 is manufactured by a continuous process during which the various layers forming the absorbent structure are laid on one another and sealed to form a continuous web 40 of sanitary napkins serially joined together. The final step of the manufacturing process, immediately prior the packaging, is to die cut the web in discrete products. Typically, the web is formed by first placing on a conveyor belt a continuous band of cover layer material. Subsequently, transfer layers overlaid by absorbent cores are deposited in a spaced apart relationship on the band of cover layer material. Finally, a band of barrier layer material is placed immediately on top of the absorbent cores and sealed to the underlying cover layer band to encapsulate the absorbent structures fully. The web is then directed to the processing station shown in FIG. 3 provided to deposit on the sanitary napkin blanks 36 (by "blanks" is meant sanitary napkins that are integrally joined to one another to form the web 40) primary release strips 30. The processing station comprises a vacuum roll provided with perforations on its circumferential surface through which a pressure differential can be established. The vacuum is effective only on the perforations that reside within the sector 42 having an annular extent of about 120°. The sector 42 creates an active suction region that causes a web to adhere to the surface of the roll 41 as it travels through that region. Outside the boundaries of the active suction region, the web is no longer retained to the roll 41.

FIG. 3A is a vertical cross-sectional view of the roll 41 and illustrates how the active suction region is implemented. The roll 41 is a hollow structure in which is mounted a stationary manifold 44 connected by a conduit 46 to a source of vacuum (not shown in the drawings). The manifold 44 has an apertured convex wall 48 closely spaced from the periphery of the drum 41 to establish a fluid communicative relationship between the source of vacuum and the perforations on the drum 41 that reside in the active region 42.

On top of the vacuum roll 41 is mounted a cutting roll 50 that rotates at the same linear speed as the vacuum roll 41. The cutting roll 50 includes a plurality of axially extending cutting blades 52 that are circumferentially spaced by a distance corresponding to the width of a primary release strip 30.

The release strip material is supplied to the nip between the cutting roll 50 and the vacuum roll 41 as a continuous web 54 drawn from a supply reel (not shown). The web of release strip material is cut by the action of the cutting roller 50 in discrete primary release strips 30 that are retained against the vacuum roll 41 as they enter the active suction region. Thus, the discrete primary release strips 30 are firmly retained against the vacuum roll 41 until they pass beyond the lower boundary of the active vacuum region where they are deposited on individual sanitary napkin blanks 36.

The primary release strips 30 provide a convenient vehicle for depositing the adhesive material forming the bands 20 and 22 on the sanitary napkin blanks 36. At this end, adhesive is applied on the silicone treated surface of the web 54 of release material between the supply reel and the nip of the rollers 50 and 41 by any suitable device such as a sprayer or a slot coater. The adhesive is a hot-melt glue well-known to those skilled in the art. H. B Fuller Canada is a supplier of a variety of hot-melt adhesive particularly well-suited for use on sanitary napkins or other sanitary absorbent articles. The adhesive is applied on the web 54 according to a pattern to suit the desired disposition of adhesive zones on the final product. In the example shown, the adhesive is deposited as transversely spaced strips to form the adhesive bands 20 and 22.

In use, the web 54 is adhesive coated then cut into successive primary release strips 30 and finally deposited on respective sanitary napkin blanks 36. During the application of each primary release strip 30 on the respective sanitary napkin blank the adhesive bands are transferred to the barrier layer and they permanently stick to it.

Note that the vacuum roll 41 is driven at a different linear speed than the sanitary napkins blanks 36 to enable the individual release strips 30, which abut one another, to register with the respective blanks 36 that are in a spaced apart relationship. At this end the vacuum roll 41 is operated stepwise rather than being rotated at a continuous speed. At each angular increment the roll is accelerated until its linear speed matches the speed of an incoming blank. Thus, while the blank 36 and the vacuum roll 41 are in contact with one another there is no slip between them to allow proper transfer of the release strip 30. After the transfer is completed the vacuum roll slows down for a short period of time before initiating a new angular increment for the next blank 36.

After this operation is completed, the web 40 is passed through a second processing station that applies the secondary release strips 32. The release strip material is supplied to the processing station as a continuous web 56, adhesive coated at spaced intervals for creating the adhesive zones 24, 26 and 34 and then pressed against the sanitary napkin blanks 36, over the primary release strips 30. The application is made by a roll 58 that has a linear speed corresponding to the speed of travel of the web 40. Contrary to the first processing station, no cutting takes place at the second processing station and as a result, there is no need to use a vacuum roll for holding discrete elements.

The next processing station, not shown in the drawings, uses a die cutting apparatus that separates the sanitary napkin blanks 36 from one another to form final products. During the cutting operation, the continuous strip 56 of release material is cut between adjacent products.

Figure 5:
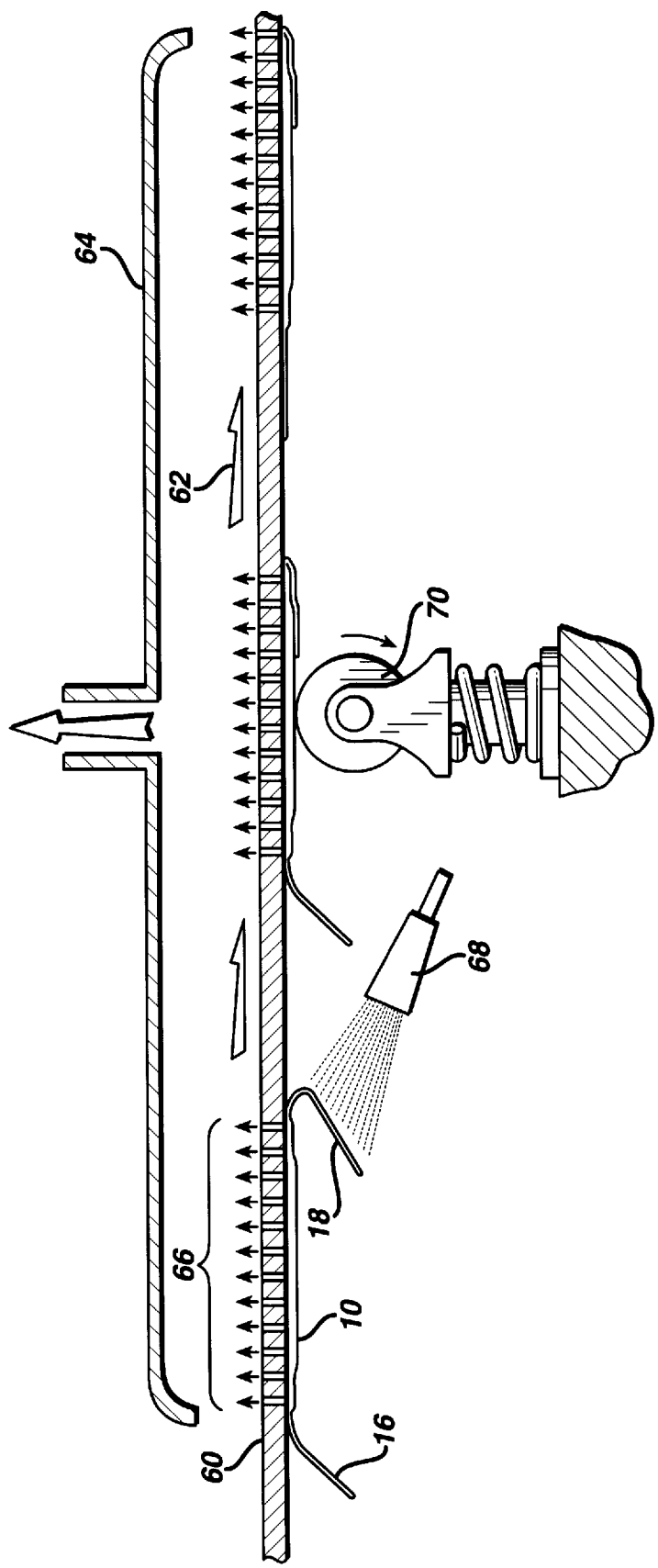
FIG. 5 is a side elevational schematic view of an apparatus for folding a tab of the sanitary napkins during a packaging operation.

This completes the manufacture of the sanitary napkins. The next operation performed on the production line is the packaging process that consists of folding the sanitary napkins 10 and then placing them in individual pouches. FIG. 5 is a schematical illustration of the first processing station of the packaging section. The processing station comprises a conveyor belt 60 that travels in the direction of the arrow 62. Above the conveyor belt 60 is provided a large suction casing 64 connected to a source of vacuum (not shown). The belt 60 has arrays 66 of perforations spaced from one another by a distance corresponding to about twice the length of a positioning tab. The perforations of a given array 66 are designed to hold by suction on the undersurface of the belt 60 a sanitary napkin by its main body and leave the positioning tabs hanging. This feature allows one positioning tab to be folded against the cover layer of the sanitary napkin as it will be described below.

An air jet 68 generates a stream of compressed air against the leading tab 18 and forces the tab to fold against the cover layer of the sanitary napkin. While the tab 18 is maintained in the folded condition by the current of compressed air, it passes through a nip formed by a creasing roll 70 and the surface of the conveyor belt 60. The roll 70 creates a significant amount of pressure to form a sharp crease in the secondary release strip 32 at the fold region between the positioning tab 18 and the main body of the sanitary napkin. Since the release strip 32 is attached to both the positioning tab 18 and the main body of the sanitary napkin, when creased the release strip, due to its inherent rigidity, will maintain the positioning tab in the folded condition.

Figure 6:
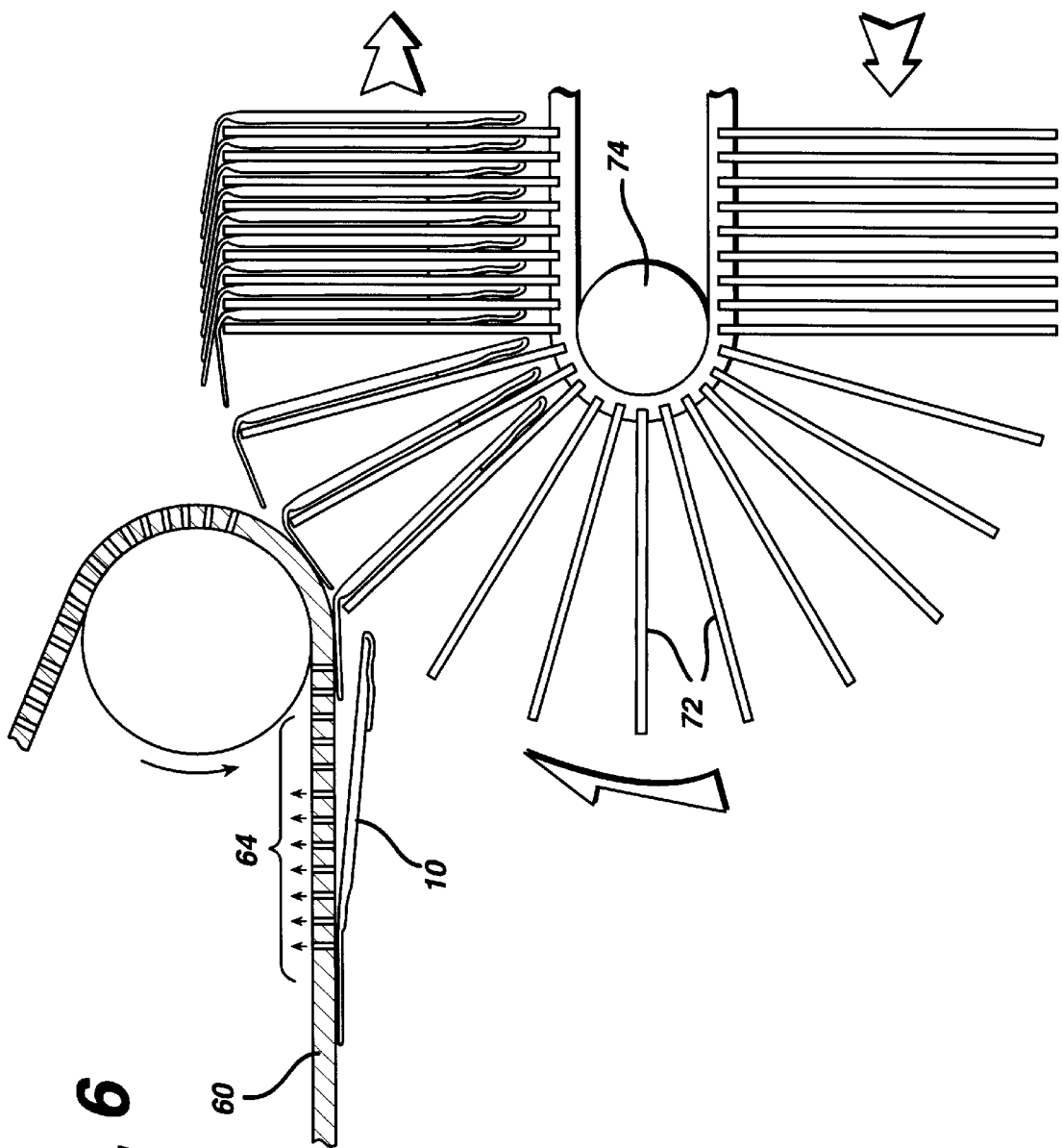
FIG. 6 is a schematical side elevational view of a device for inverting the sanitary napkins during the packaging operation.
Figure 7:
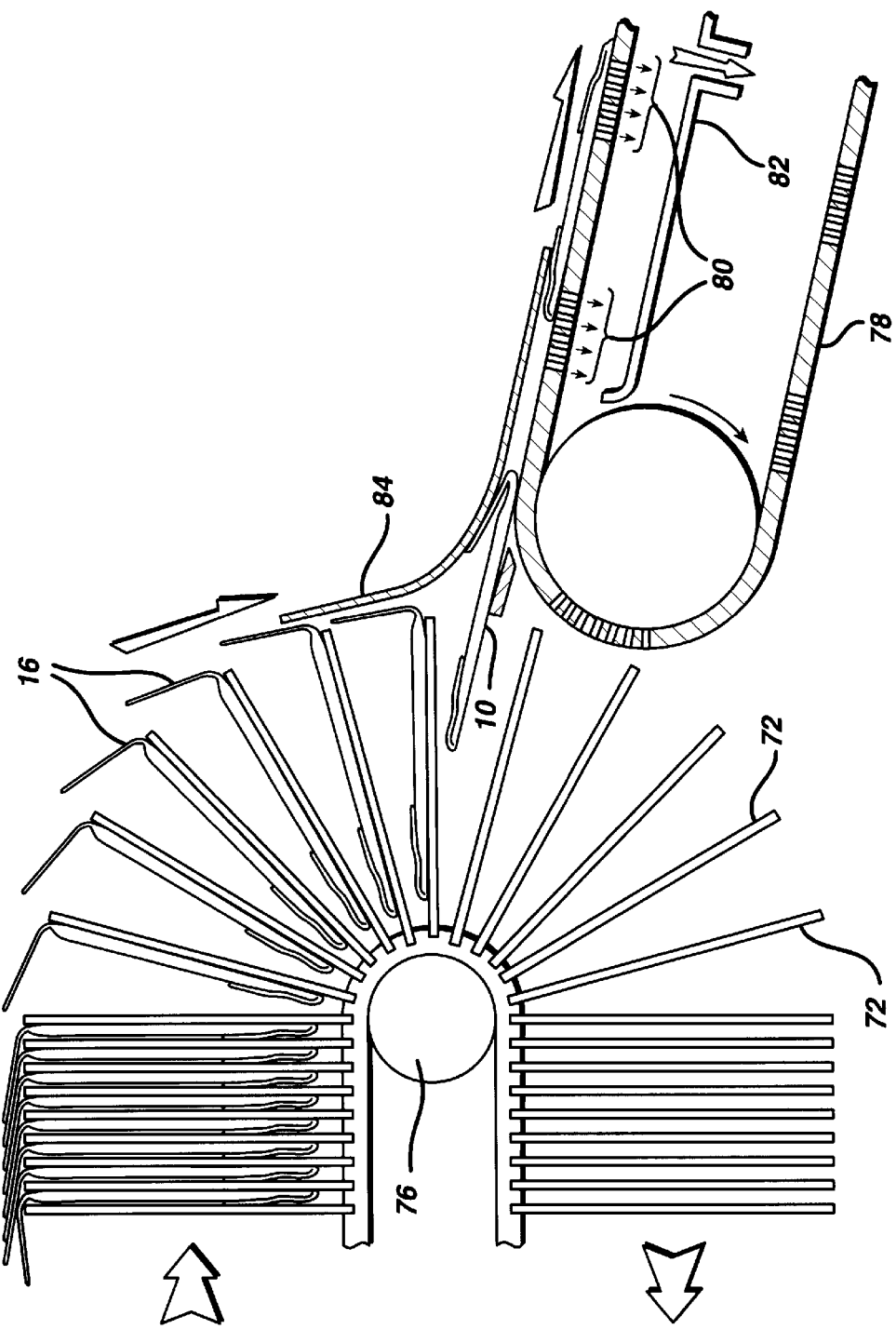
FIG. 7 is a side elevational schematic view illustrating the sanitary napkins when released from the inverting device.

The next processing station of the packaging section is shown in FIGS. 6 and 7 and comprises an inverter designed to flip the sanitary napkins upside down. In other words, the sanitary napkins will be returned so their cover layers face up. The inverter is an endless conveyor belt with projecting slats 72 that define sanitary napkin holding pockets between them. The conveyor belt 60 ends its horizontal run where the conveyor belt of the inverter loops a roller 74 so the sanitary napkin holding pockets are wide open. When the individual sanitary napkins 10 pass beyond the vacuum region created by the suction casing 64, they are released from the conveyor belt 60 and enter respective holding pockets of the inverter.

Figure 8:
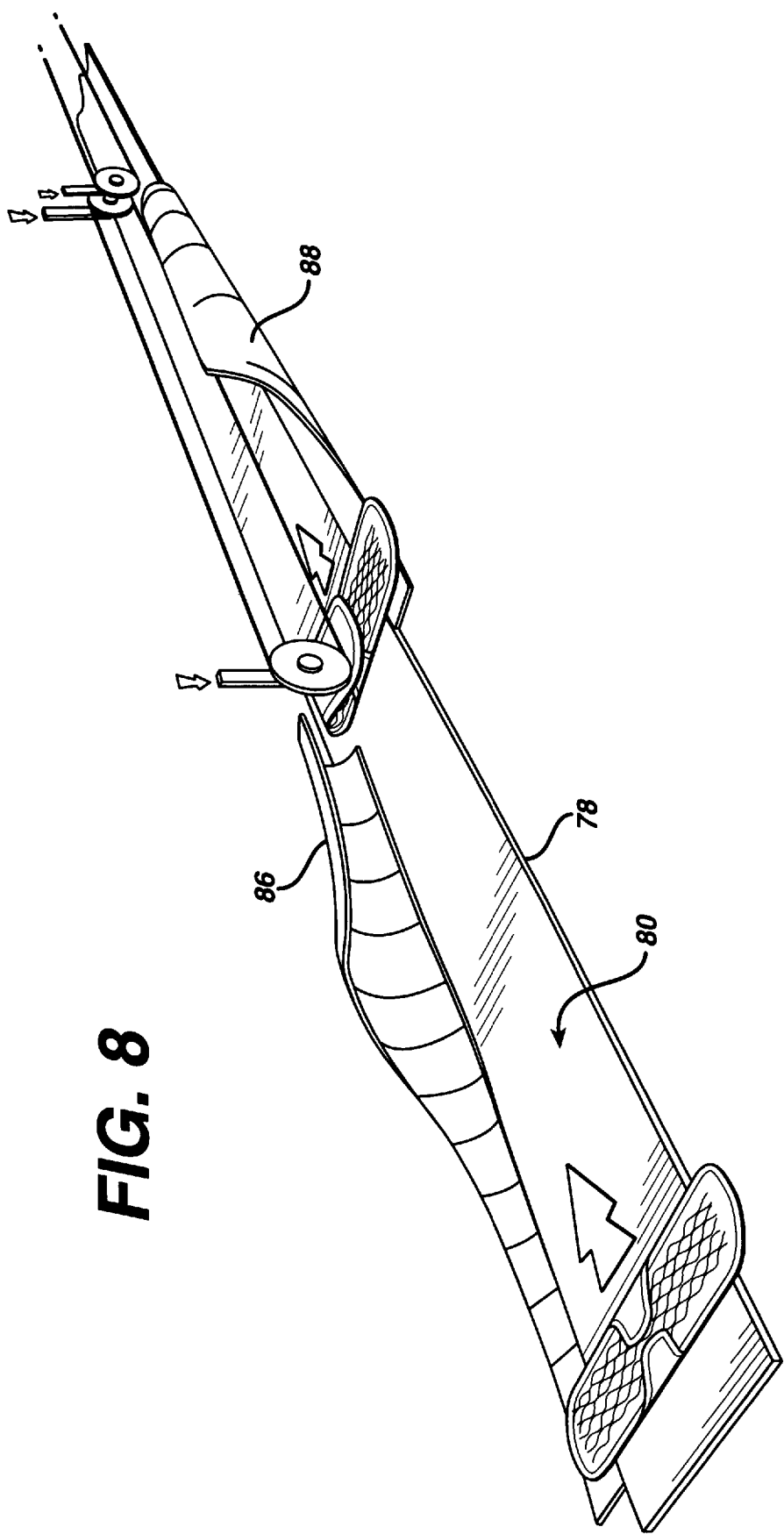
FIG. 8 is a perspective view of the device for completing the folding operation of the sanitary napkin.

The sanitary napkins 10 travel horizontally on the inverter until they reach a roller 76 that is looped by the conveyor belt. At this point, the slats 72 are spread apart so the individual sanitary napkins are free to egress the pockets and fall on a third conveyor belt 78 that is similar to the conveyor belt 60 in that it comprises arrays 80 of apertures passing under a suction casing 82 to grip by the effect of vacuum the sanitary napkins 10 by the main body. FIG. 8 illustrates the arrangement of the perforations of a single array 80. It will be noted that the perforations are concentrated in the central portion of the conveyor belt 78 so that only the central portion of the main body will be subjected to vacuum. This allows the longitudinal extremities and the positioning tabs to be folded as it will be described later.

As the sanitary napkins 10 are discharged from the inverter, they pass under a guide 84 whose purpose is to fold the positioning tab 16. The guide 84 is a curved plate that converges toward the conveyor belt 78 to fold the positioning tabs 16 progressively and also crease the secondary release strip 32 at the juncture between the tab 16 and the main body of the napkin. The pressure exerted on the sanitary napkin increases significantly when the tail end of the guide 84 is reached which causes the release strip 32 to crease which will hold the tab 16 folded until the packaging operation is completed.

It will be noted that the release tab 18 is unlikely to unfold as the sanitary napkin passes between the progressively narrowing passage of the guide 84 because the tab 18 is maintained in a tightly folded condition by the creased release strip 32.

The sanitary napkins 10 leaving the guide 84 are in the form shown in FIG. 8, with both of their flaps folded against the body contacting cover layer. The next step of the folding operation is to pass the sanitary napkin through longitudinally extending guides 86 and 88 that gradually curve the longitudinal extremities of the sanitary napkin so as to progressively fold them against the cover layer. At this point, the pouch is formed around the sanitary napkin so as to provide a protective envelope to prevent contamination of the product during shipping and storage. The method and the apparatus used for forming the individual pouches will not be described herein because they are well known in the industry and they do not form part of the present invention.

In a possible variant, the order of placement of the release strips 30 and 32 is reversed so the larger release strip 30 is on top of the smaller release strip 32. This embodiment is suitable for applications where it is desirable to effect removal of the entire peelable protective layer by pulling on the strip that covers the adhesive zones 24, 26 on the positioning tabs 16, 18, respectively. To manufacture this variant, the process as described earlier is followed except that the processing station applying the secondary release strip 32 is placed before the processing station that applies the primary release strip 30.

Figure 9:
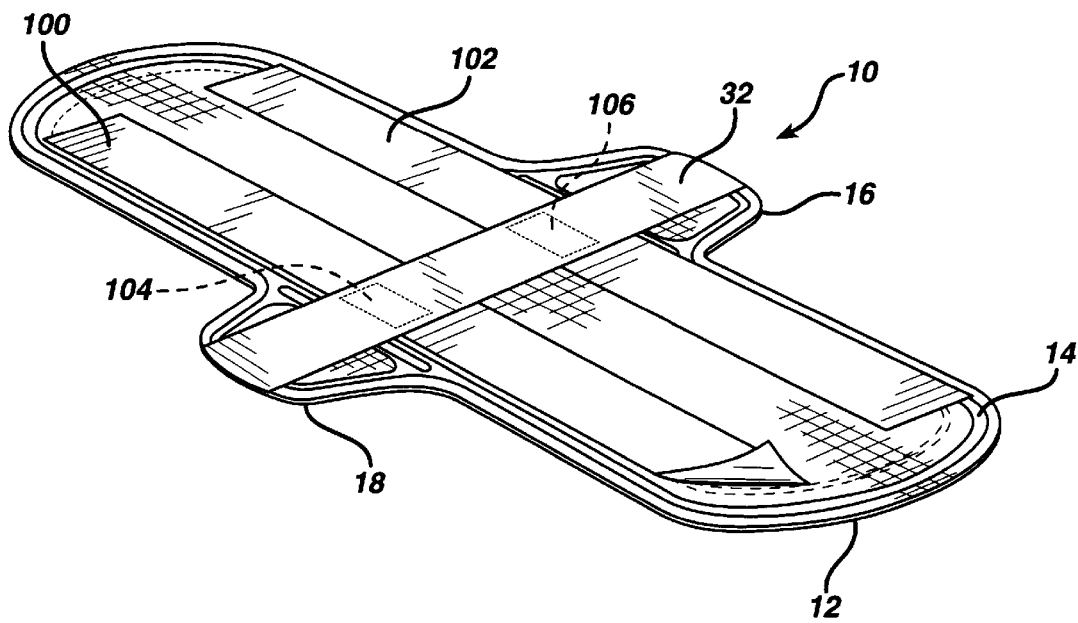
FIG. 9 is a perspective view of a sanitary napkin constructed in accordance with a variant.

In a further variant two smaller release strips, covering the respective adhesive bands 20, 22 could be substituted to the main release strip 30 for reducing the amount of release strip material required to cover the adhesive system. This embodiment is shown in FIG. 9. The smaller release strips that replace the single release strip 30 are designated by the reference numerals 100 and 102. To manufacture this embodiment, two changes are required. First, the cutting roll 50 is provided with additional cutting blades 52 so the web 54 is severed into narrower strips. Second, the adhesive deposition pattern on the web 56 is modified so each secondary release strip 32 bonds with each one of the strips 100 and 102 at 104 and 106.

Applications of the product, method and apparatus of the present invention for sanitary and other health-care uses can be accomplished by any sanitary protection, incontinence, medical and absorbent methods and techniques as are presently or perspectively known to those skilled in the art. Thus, it is intended that the present application covers the modifications and variations of this invention provided that they come within the scope of the appended claims and their equivalents.

I claim:

1. A disposable sanitary absorbent article for adhesive securement to an undergarment of a wearer, said absorbent article comprising:
   a main body that includes:
      a) a body contacting liquid-pervious cover layer;
      b) an absorbent core underneath said body contacting liquid-pervious cover layer, said absorbent core being in liquid-communicative relationship with said cover layer, whereby liquid discharged on said cover layer is transferred to said absorbent core for storage therein;
      c) a liquid-impervious barrier layer beneath said absorbent core, said barrier layer preventing liquid entrapped in said absorbent core from egressing said main body from a garment facing surface thereof;
   a positioning tab laterally projecting from respective longitudinal sides of said main body, each said tab being flexible and being capable of being folded about a respective edge of the undergarment on which said absorbent article is to be installed;
   an adhesive securement system for releasably retaining said absorbent article to the undergarment, said adhesive securement system including;
      a) a first adhesive zone on the undergarment facing surface of said main body;
      b) a second adhesive zone on the undergarment facing surface of one of said positioning tabs;
      c) a third adhesive zone on the undergarment facing surface of the other one of said positioning tabs, said first, second and third adhesive zones being in a spaced apart relationship;
      d) a peelable protective layer covering said adhesive zones, said peelable protective layer being removable from said absorbent article and including:
         i) a primary release strip extending generally longitudinally on said main body and being releasably attached to said first adhesive zone;
         ii) a secondary release strip extending generally transversely on said main body and having a transverse dimension sufficient to span from one of said laterally projecting positioning tabs across said main body to the other one of said laterally projecting positioning tabs and being releasably attached to said second and third adhesive zones, said release strips crossing each other.

2. A disposable sanitary absorbent article as defined in claim 1, wherein said primary release strip is linked to said secondary release strip.

3. A disposable sanitary absorbent article as defined in claim 2, wherein said primary release strip is adhesively connected to said secondary release strip at a crossing point between said strips.

4. A disposable sanitary absorbent article as defined in claim 1, wherein said secondary release strip overlays a garment facing surface of said primary release strip.

5. A disposable sanitary absorbent article as defined in claim 1, wherein said primary release strip overlays a garment facing surface of said secondary release strip.

6. A disposable sanitary absorbent article as defined in claim 1, wherein said first adhesive zone comprises a plurality of adhesive zones on said main body that are in a spaced apart relationship, said primary release strip having dimensions sufficient to cover said plurality of adhesive zones.

7. A disposable sanitary absorbent article as defined in claim 6, wherein said first adhesive zone comprises a plurality of longitudinally extending adhesive bands, said primary release strip having a transverse dimension sufficient to span said longitudinally extending adhesive bands.

8. A disposable sanitary absorbent article as defined in claim 1, comprising:
   a fourth adhesive zone on said main body; and
   a release strip other than said primary and secondary release strips releasably attached to said fourth adhesive zone.

9. A disposable sanitary absorbent article as defined in claim 8, wherein said secondary release strip crosses said release strip other than said primary and secondary release strips.

10. A disposable sanitary absorbent article as defined in claim 8, wherein said primary release strip and said release strip other than said primary and secondary release strips are in the form of longitudinally extending bands that are spaced from one another.

11. A disposable sanitary absorbent article as defined in claim 1, wherein said release strips comprise paper material having a non-stick surface.

12. A sanitary absorbent article according to claim 1 wherein said sanitary absorbent article is in a folded condition and wherein said secondary release strip includes a crease in a folded region of said sanitary absorbent article, said secondary release strip manifesting a shape retention capability when creased, whereby said secondary release strip assists said sanitary absorbent article in maintaining a folded condition by resisting efforts tending to increase said secondary release strip.

13. A sanitary absorbent article as defined in claim 12, wherein two creases are formed in the folded region of said sanitary absorbent article said creases being formed between said second adhesive zone and the longitudinal side of the main body and between said third adhesive zone and the longitudinal side of the main body.

14. A sanitary absorbent article as defined in claim 12, wherein said second adhesive zone and said third adhesive zone are in a spaced apart relationship, said secondary release strip covering said zones, said crease being formed between said zones.

15. A sanitary absorbent article as defined in claim 12, wherein said folded region is located approximately at the juncture between the positioning tab of said sanitary absorbent article and the main body of said sanitary absorbent article.

16. A sanitary absorbent article as defined in claim 12, wherein said secondary release strip includes paper material.

17. A sanitary absorbent article comprising:
   a main body further comprising:
      a) a body contacting liquid-pervious cover layer;
      b) an absorbent core underneath said body contacting liquid-pervious cover layer, said absorbent core being in liquid-communicative relationship with said cover layer, whereby liquid discharged on said cover layer is transferred to said absorbent core for storage therein;
      c) a liquid-impervious barrier layer beneath said absorbent core, said barrier layer preventing liquid entrapped in said absorbent core from egressing said main body from a garment facing surface thereof;

d) at least one positioning tab extending laterally from a longitudinal side of said main body of said sanitary absorbent article; and e) a release strip covering an adhesive zone of said sanitary absorbent article, said release strip extending over a juncture between said positioning tab and said main body;

wherein said positioning tab is folded over the body contacting liquid-pervious cover layer and said release strip is folded at said juncture and manifesting a sufficient shape retention capability for resisting efforts tending to unfold said positioning tab.

18. A sanitary absorbent article as defined in claim 17, wherein said release strip is creased at said juncture.

19. A sanitary absorbent article as defined in claim 18, wherein said release strip includes paper material.

* * * * *